United States Patent [19]

Rink et al.

[11] Patent Number: 4,994,060

[45] Date of Patent: Feb. 19, 1991

[54] LASER HEATED CAUTERY CAP WITH TRANSPARENT SUBSTRATE

[75] Inventors: Dan L. Rink, Oakland; John L. Rink, San Francisco; Garrett Lee, Piermont, all of Calif.

[73] Assignee: Xintec Corporation, Oakland, Calif.

[21] Appl. No.: 325,955

[22] Filed: Mar. 20, 1989

Related U.S. Application Data

[63] Continuation-in-part of Ser. No. 179,678, Apr. 11, 1988, Pat. No. 4,848,339, which is a continuation-in-part of Ser. No. 19,755, Feb. 27, 1987, which is a continuation-in-part of Ser. No. 650,889, Sep. 17, 1984.

[51] Int. Cl.$^5$ .............................................. A61B 17/36
[52] U.S. Cl. ........................................ 606/28; 606/7; 606/15; 128/398
[58] Field of Search ...................... 128/303.1, 397, 398, 128/399, 400, 401; 606/7, 10, 13–19, 27, 28, 31; 219/121.6, 121.65, 121.66, 121.73, 121.74, 121.75, 229, 233, 236–239, 243, 244

[56] References Cited

U.S. PATENT DOCUMENTS

| | | | |
|---|---|---|---|
| 4,445,892 | 5/1984 | Hussein et al. | 606/7 |
| 4,449,528 | 5/1984 | Auth et al. | 606/31 |
| 4,648,892 | 3/1987 | Kittrell et al. | 128/398 |
| 4,654,024 | 3/1987 | Crittenden et al. | 606/28 |
| 4,662,368 | 5/1987 | Hussein et al. | 606/7 |
| 4,672,961 | 6/1987 | Davies | 606/7 |
| 4,672,962 | 6/1987 | Hershenson | 128/401 |
| 4,676,231 | 6/1987 | Hisazumi et al. | 606/14 |
| 4,740,047 | 4/1988 | Abe et al. | 606/2 |
| 4,754,752 | 7/1988 | Ginsberg et al. | 606/7 |
| 4,848,339 | 7/1989 | Rink et al. | 606/16 |

FOREIGN PATENT DOCUMENTS 2826383 12/1979 Fed. Rep. of Germany ... 128/303.1

OTHER PUBLICATIONS

"Laser Radiation of Artherosclerotic Lesions . . . ", by Sanborn et al.; JACC Abstracts; vol. 3, No. 2, Feb. 1984, p. 490.

*Primary Examiner*—Lee S. Cohen
*Assistant Examiner*—David Shay
*Attorney, Agent, or Firm*—Howard Cohen

[57] ABSTRACT

A laser heated cautery cap assembly includes a catheter assembly adapted to be introduced into a lumen, such as an arterial opening. The catheter assembly includes at least one optical fiber connected to a laser light source adapted to produce short output bursts. A cautery cap at the catheter distal end includes a transparent substrate member disposed to receive the laser energy from the optical fiber(s). The substrate member preferably is formed of a crystalline solid having a smooth, curved outer surface, with a central guidewire bore extending therethrough. One end of the bore is provided with a tapering counterbore, and the opposite end of the substrate member is an input surface disposed to receive laser energy from the optical fiber. A nose piece includes a central guidewire bore coaxial with the substrate member bore, the nose piece including a tapered proximal end dimensioned to fit within the counterbore of the substrate. The substrate counterbore and bore surfaces, and major portions of the curved outer surface are coated with a highly reflective material, and another portion of the outer surface is coated with a material which absorbs the laser energy and is heated thereby. The input surface of the substrate receives laser illumination from the optical fiber(s) and conducts it to the counterbore surface, which reflects the light internally to the absorptive coating portion. Thus a portion of the cap structure is heated, while the nose piece and the remainder of the substrate surface remains relatively cool.

35 Claims, 5 Drawing Sheets

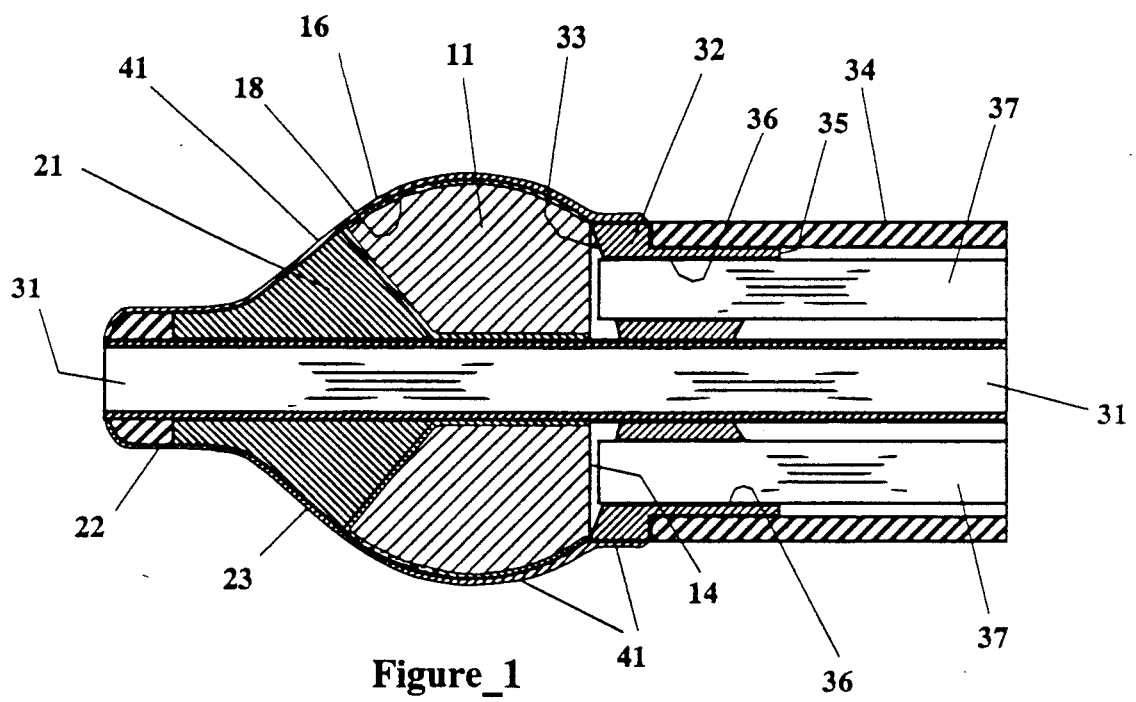
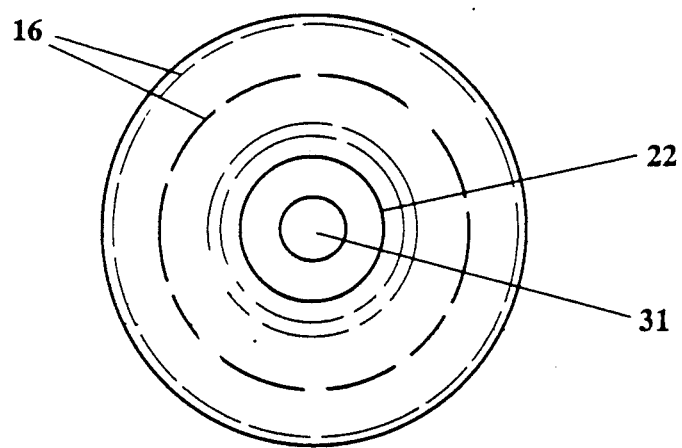

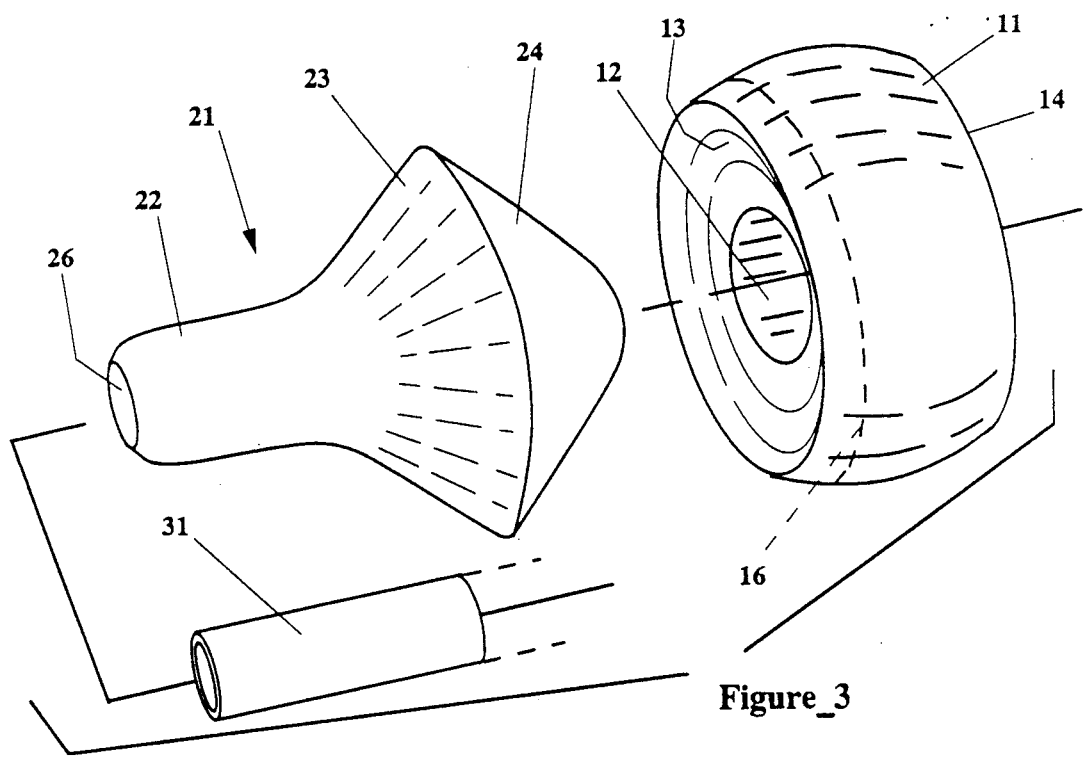
Figure_3
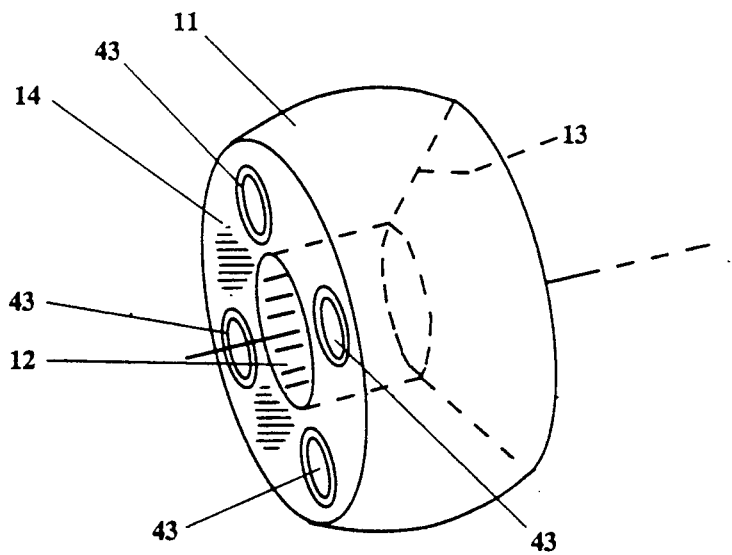
Figure_5

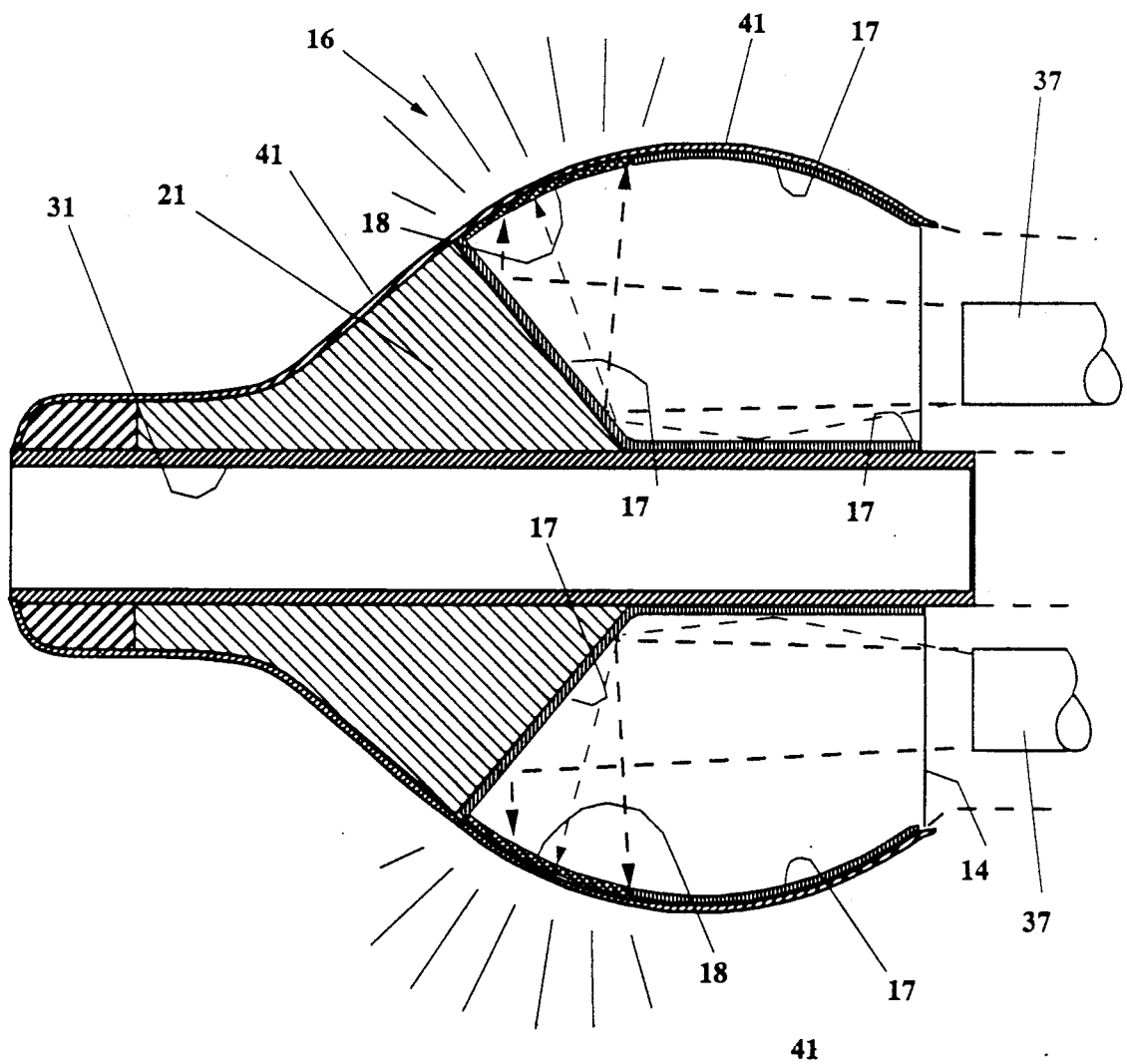
Figure_4

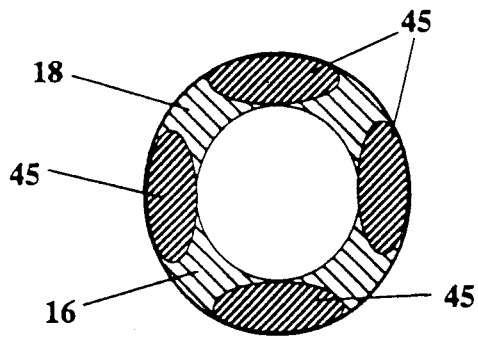
Figure_6
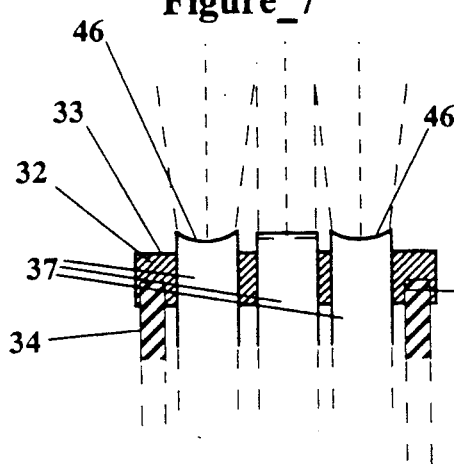
Figure_7
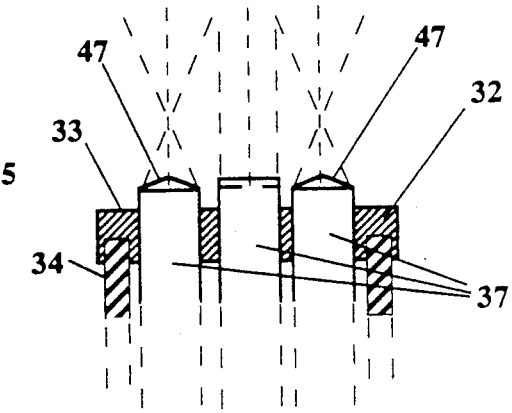
Figure_8
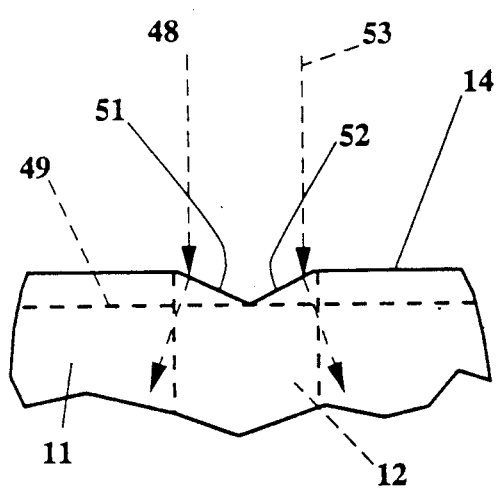
Figure_9
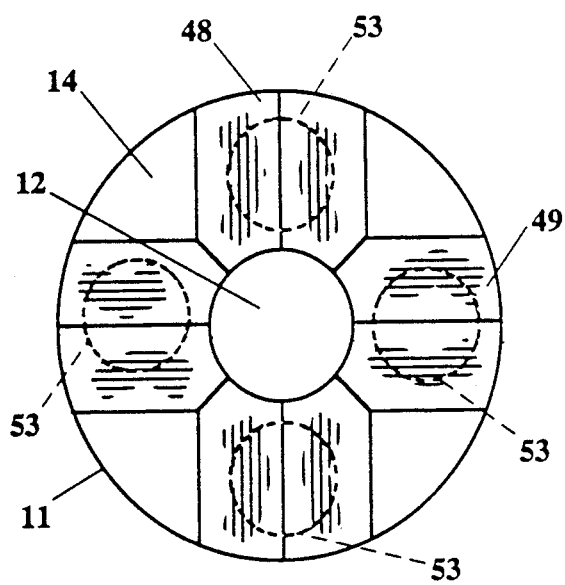
Figure_10

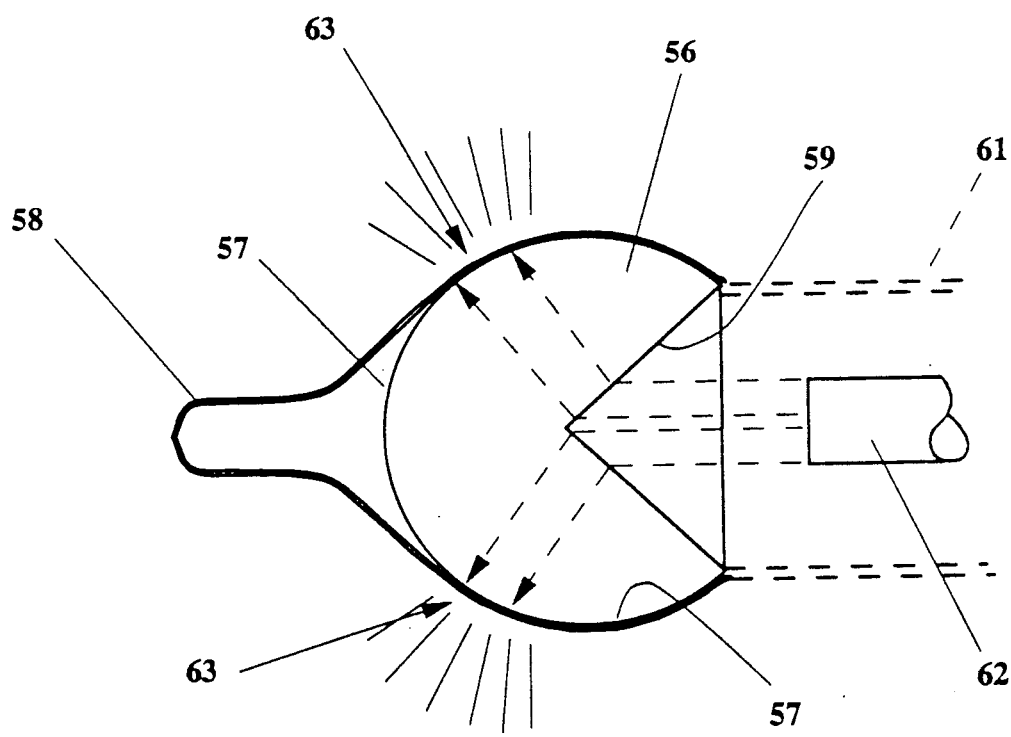
Figure_11

4,994,060

LASER HEATED CAUTERY CAP WITH TRANSPARENT SUBSTRATE

REFERENCE TO RELATED APPLICATION

This application is a continuation-in-part of U.S. patent applicaton Ser. No. 07/179,678, filed Apr. 11, 1988 by the present inventors now Pat. No. 4,848,339, which is a continuation-in-part of application Ser. No. 07/019,755, filed Feb. 27, 1987, which in turn is a continuation-in-part of application Ser. No. 06/650,889, filed Sept. 17, 1984, for which priority is claimed.

BACKGROUND OF THE INVENTION

In recent research carried out in recanalization of atherosclerotic vessels, the laser heated cautery cap has been proven as an effective tool in reopening stenotic vessels. Moreover, it has been demonstrated that atherosclerotic plaque can be removed by attacking it with a laser heated cautery cap that is heated briefly and reiteratively to a high temperature sufficient to thermally destroy the plaque material. In this approach a brief thermal pulse delivered to the plaque destroys the plaque in contact with the cap before the heat can flow to the arterial walls, so that damage to the vessel is minimized or eliminated.

The brief, high temperature thermal pulse can be delivered only by a laser heated cautery cap having a small thermal mass, so that heating and cooling of the cap is accelerated to the maximum extent. However, reduction of the thermal mass in a conventional cautery cap requires that less physical mass is present, and there is a limit to the amount of cap mass that can be eliminated before structural problems occur. For example, the cap wall thickness cannot be reduced below the minimum required to prevent collapse of the cap. Moreover, reduction in the cap mass generally requires smaller cap parts, which exacerbates assembly and manufacturing problems.

It has also been found that the best results are achieved in recanalization by laser heating cautery cap if the high temperature thermal pulse can be localized in the cap areas that are in contact with the plaque, while preventing thermal flow to the remainder of the cap. This requirement has been met in the prior art by multiple fiber catheter assemblies, with each fiber heating a discrete portion of the cap. However, directing the laser energy solely to the leading shoulder area of the cap which generally contacts the plaque, while avoiding unacceptable heating of the vessel wall, is a goal that is not always attained in prior art cautery cap structures.

The related patent application noted above describes one solution to the problems discussed above, in that it describes a laser heated cautery cap formed by a transparent substrate and outer layer applied directly to the substrate surface by deposition techniques. The transparent substrate is a crystalline solid, such as sapphire, that is highly transparent to the optimum laser type for this field (NdYAG), rugged and dimensionally stable over a high temperature range, easily machined and surfaced, and is a thermal insulator. Portions of the substrate are coated to absorb the laser light received from a plurality of optical fibers, while the remaining portions are coated with a highly reflective coating to keep all laser light captive and to minimize surface heating of these remaining portions. The present invention includes improvements in these concepts, as well as new structural and functional additions.

SUMMARY OF THE PRESENT INVENTION

The present invention generally comprises a laser heated cautery cap assembly which includes a transparent substrate on which the cautery cap walls are formed by thin film deposition techniques. The thin film walls comprise the minimum physical mass required to absorb and transform laser light energy into thermal energy, providing the lowest possible thermal mass and the fastest temperature rise time and fall time. Also, the present invention provides a controlled, vectorized heating of only selected portions of the cautery cap, while maintaining a coolnose tip. And, the invention provides an alternative embodiment in which the laser illumination is spread angularly to provide broader coverage and more uniform heating of the selected heated zone.

The laser heated cautery cap and catheter assembly includes at least one optical fiber connected to a laser light source adapted to produce short output burst. A cautery cap at the catheter distal end includes a transparent substrate member disposed to receive the laser energy from the optical fiber(s). The substrate member preferably is formed of a crystalline solid having a smooth, curved outer surface, with a central guidewire bore extending therethrough. One end of the bore is provided with a tapering counterbore, and the opposite end of the substrate member is an input surface disposed to receive laser energy from the optical fiber. A nose piece includes a central guidewire bore coaxial with the substrate member bore, the nose piece including a tapered proximal end dimensioned to fit within the counterbore of the substrate. The substrate counterbore and bore surfaces, and major portions of the curved outer surface are coated with a highly reflective material, and another portion of the outer surface is coated with a material which absorbs the laser energy and is heated thereby. The input surface of the substrate receives laser illumination from the optical fiber(s) and conducts it to the counterbore surface, which reflects the light internally of the absorptive coating portion. Thus a portion of the cap structure is heated, while the nose piece and the remainder of the substrate surface remains relatively cool. The input surface may be provided with a plurality of optically shaped surfaces, each disposed to receive the laser illumination from one optical fiber. Each optically shaped surface includes a surface configuration to spread the incoming laser beam angularly about the axis of the device to broaden the heated portion of the absorptive layer.

Alternatively, the optical fiber ends may be provided with shaped surfaces to spread each beam emanating from the respective fiber end, the beam diverging only in a direction to encompass a larger peripheral portion of the band of absorptive material.

BRIEF DESCRIPTION OF THE DRAWING

FIG. 1 is a cross-sectional side view of the laser heated cautery cap of the present invention.

FIG. 2 is a distal end view of the laser heated cautery cap shown in FIG. 1.

FIG. 3 is an exploded perspective view of the transparent substrate and nosepiece assembly of the present invention.

FIG. 4 is an enlarged cross-sectional elevation of the cautery cap assembly, showing the essential light paths within the substrate.

FIG. 5 is a perspective view of an alternative embodiment of the transparent substrate of the invention.

FIG. 6 is an end view of the annular band of absorptive material of the cautery cap, showing a pattern of enhanced laser beam spreading in the peripheral direction.

FIG. 7 is a cross-sectional side elevation of an alternative embodiment of the invention in which the ends of the optical fibers are shaped to spread the laser beams emanating therefrom to encompass a larger peripheral portion of the absorptive band.

FIG. 8 is a cross-sectional side elevation of a further embodiment of the invention in which the ends of the optical fibers are shaped to spread the laser beams emanating therefrom to encompass a larger peripheral portion of the absorptive band.

FIG. 9 is a fragmentary view of an alternative embodiment of the substrate member of the invention, in which the input surface is shaped to spread the laser beams impinging thereon to encompass a larger peripheral portion of the absorptive band.

FIG. 10 is an end view of the alternative substrate member shown in FIG. 9.

FIG. 11 is a cross-sectional view of a further embodiment of the present invention, in which a transparent substrate is illuminated and heated by a single optical fiber.

DESCRIPTION OF THE PREFERRED EMBODIMENT

With regard to FIGS. 1-4 of the accompanying drawing, one embodiment of the present invention includes a transparent substrate member 11, formed of a crystalline solid material that is highly transparent to laser light, strong and stable at high temperatures, and is a good thermal insulator. One such material is sapphire, though other such materials may be substituted. The member 11 is formed with a smooth outer surface in a closed curved configuration, such as a sphere, ellipsoid, prolate spheroid, or the like. A central bore 12 extends through the member 11 coaxial with the outer surface configuration.

The distal end of the member 11 is provided with a counterbore 13 concentric with the bore 12 and tapering therein to form a cavity as a right truncated cone. The surface 13 is smooth and polished, as are the other surfaces of the member 11. At the opposite, proximal end of the member 11, the end surface 14 is formed as a smooth plane generally perpendicular to the axis of the bore 12. It is significant that virtually the entire surface of the member 11, with the exception of the band 16 and the end surface 14, is coated with a thin layer 17 of a highly reflective material, such as gold, silver, or the like, as shown in FIG. 4. The layer 17 may be applied using common industrial and integrated circuit thin film techniques, such as electrodeposition, plating, dipping, chemical vapor deposition, metallorganic vapor deposition, mechanical keying, or the like. It may be appreciated that the transparency of the substrate member and the high reflectivity layer 17 combine to permit not only transmission but also internal reflection of laser light introduced into the substrate member through the planar rear face 14.

The band 16 is coated with a layer 18 of material that is highly absorptive of the laser light energy. The absorptive material, such as copper, copper oxide or the like also has low reactivity and high thermal conductivity. The layer 18 may be formed by plating, dipping, chemical vapor deposition, metallorganic vapor deposition, mechanical keying, or other thin film techniques. The layer 18 extends throughout the annular band 16, which is disposed at the distal end of the substrate member adjacent to the reflective surface 17.

The cautery cap assembly also includes a nose piece 21 adapted to be joined to the substrate member 11. The nose piece 21 includes a distal end portion 22 having a generally cylindrical outer configuration with a small diameter compared to the substrate member and a slightly rounded distal end. A medial portion 23 of the nose piece extends proximally from the proximal end of the portion 22, and is configured to flare outwardly toward the proximal direction in a smoothly curving compound surface configuration. The proximal end portion 24 of the nose piece extends from the widest part of the portion 23, and includes an outer surface formed as a right truncated cone dimensioned to be received within the counterbore 13 in a minimum clearance fit.

The nose piece 21 is formed of an inert material, such as stainless steel, ceramic, aluminum, or the like, and includes a bore 26 extending therethrough. As shown in FIGS. 1 and 4, the bores 12 and 26 are in axial alignment when the proximal end of the nose piece is received in the counterbore 13. A sleeve member 31 extends through the aligned bores 12 and 26 to form a lined, continuous opening through which an arterial guide wire may be extruded. The sleeve member also maintains the primary assembly of the nose piece and the substrate member.

The cautery cap assembly also includes a connector member 32, which is a bushing-like member having a central bore therein through which the sleeve member 31 extends. The connector member 32 includes a distal end face 33 disposed in closely adjacent, confronting relationship to the planar end 14 of the substrate member. A reduced diameter neck 35 extends proximally, and is dimensioned to receive the distal end of an arterial catheter tube 34. The connector member is also provided with a plurality of holes 36 extending therethrough parallel to the bore and sleeve 31, and spaced equally thereabout. Each of the holes 36 is dimensioned to accept the distal end of an optical fiber 37 in close tolerance fit, and to be secured therein by adhesive or the like. The connector member may be formed of brass, stainless steel, or the equivalent. As before, the sleeve 31 aids in maintaining the assembly of the connector member to the nose piece and substrate member.

The entire outer surface of the assembled components 11, 21, and 32 is preferably coated with a unitary layer 41 of the durable, heat conductive material, such as nickel. The layer 41 may be electroformed, in the case of nickel, or dipped, plated, or deposited as is appropriate to the material chosen. The layer 41 forms a smooth, continuous outer surface, and also acts to maintain the mechanical assembly of the components. The gap between the distal end face 33 of the connector member and the planar end 14 of the substrate member may be filled with air or inert gas, or with a transparent liquid, gel, or solid which has an index of refraction intermediate of the indices of refraction of the optical fiber and the substrate member, so that the maximum amount of laser light may be conducted into the substrate member.

With regard to FIG. 4, the laser light from the optical fibers 37 enters the planar face 14 on paths generally parallel to the sleeve 31 and directed toward the internally reflective surface of the counterbore 13. The counterbore surface is disposed to reflect the laser illumination to the band 16, where it is absorbed by the layer 18 and converted to thermal energy. This energy is conducted through the outer layer 41 to heat plaque material in contact therewith. The angle of the counterbore surface and the placement of the band 16 are selected so that the band receives the reflected laser energy, and the depiction in the Figures is only one of many possibilities. Any laser light not received by the and 16 strikes the outer surface or the bore surface coatings, both of which are internally reflective. Thus this errant light is re-reflected, so that well over 99% of the laser light is converted to heat by the material 18 in the band 16.

It is significant to note that the layer 18 (and the adhering portion of the layer 41) is extremely thin, being deposited by thin film deposition techniques. Only this material is heated to a considerable temperature, and the thermal mass that is heated is an irreducible minimum. Furthermore, the substrate material is an extremely good insulator, so that very little heat energy is absorbed in the substrate. As a result, a brief laser pulse of a fraction of a second at a power of approximately 10 watts can heat the band 16 to a temperature of several hundred degrees Celsius, hot enough to thermally destroy plaque material in contact therewith and form a crater therein. However, the thermal mass is so small, and the laser pulse sufficiently brief, that the high temperature dissipates before thermal conduction to other portions of the cautery cap can take place. As a result, the nose piece 21 remains cool, as does the proximal outer surface of the substrate member.

It should be noted also that the bore 12 of the substrate member is protected from heating by the layer 17, and that the layer 17 together with the sleeve 31 act to protect an arterial guide wire in the sleeve 31 from thermal damage from the cap itself. It is desirable to fire the laser to heat the band 16 in a reiterative manner, so that the cap may be advanced into the crater formed by a previous laser pulse, fired once again, advanced, etc., until a recanalized lumen is formed through the atherosclerotic blockage. The provision of a narrow distal nose tip which remains cool is a major advantage over the prior art, in that the narrow tip tends to seek any opening which remains in the atherosclerotic accretion. This feature significantly aids in directing the cautery cap through vessels that are completely occluded by plaque, and centering the cap within the vessel so that damage to the vessel wall is avoided.

In contrast to the band 16, the nose piece 21 comprises a relatively large thermal mass. Although the nose piece receives no laser energy directly, there heat conducted to the nose piece from the interface 13-24 and through the outer layer 41 from the heated band 16. In the large thermal mass of the nose piece, the brief, high temperature pulses are quickly dissipated before the nose piece undergoes any significant temperature increase. Indeed, a slightly warmed nose piece enhances the ability of the cap tip to seek and follow the center of the vessel. However, it should be noted that the nose piece can be fashioned as a hollow housing having the same outer configuration as shown in the Figures, without adversely affecting the performance of the cap assembly.

The placement of the band 16 distally of the widest portion of the cautery cap, and tapering toward the distal end (as shown in FIG. 2), enhances the ability of the cap of the present invention to tunnel through atherosclerotic masses, forming a lumen for itself as it progresses through the blockage. Moreover, it may be appreciated that each of the optical fibers 37 may be used separately or in combination with selected other fibers 37 to heat only angular segments of the band 16 to treat eccentric atherosclerotic lesions, as explained in the parent patent application noted above.

A major advantage of the invention is that the structure is designed for minimum handling and easy assembly, these factors being extremely important for an assembly that is generally between 1.0 mm and 3.0 mm in diameter. The substrate member may be formed as a blank by jewelers techniques, and plated or coated by well-known processes in large batches. The substrate member, nose piece, and connector member are all centered and aligned by the sleeve member 31, which also is the primary structural component for the assembly, creating a simple assembly situation. Likewise, the outer layer 41 is formed by commonly available plating or deposition techniques, and very little manual labor is required to complete the assembly.

In a further embodiment of the invention, shown in FIG. 5, the substrate member 11 is provided with a plurality of optically shaped surfaces 43, each disposed to be in confronting alignment with one of the optical fibers 37. Each optically shaped surface 43 is adapted to receive the laser illumination from the respective optical fiber 37. Each optically shaped surface 43 is provided with a configuration that is formed so that the incoming beam from the optical fiber is spread in a wider angle about the axis of the device. The reflected diverging beam strikes the band 16 throughout a larger angular portion thereof, so that a wider annular segment of the band 16 is heated by each optical fiber, as shown at reference numerals 45 in FIG. 6. This feature permits more uniform heating throughout the band 16, without sacrificing the vectorized heating capability of each optical fiber used solely or in various spatial or temporal subcombinations. A preferred device for directing the laser energy to the optical fibers in such a manner is described in U.S. patent application Ser. No. 07/180,950, filed Apr. 11, 1988, now U.S. Pat. No. 4,425,265, issued May 15, 1990, to the present inventors.

With regard to FIGS. 7 and 8, a further embodiment of the invention for spreading the laser beams emanating from the optical fibers 37 includes an optically shaped surface formed at each distal end of the optical fibers 37. In FIG. 7 each fiber end is provided with a concave surface 46 which acts as a minus lens to spread the light beam emanating therefrom. The concave surface 46 is formed as a cylindrical surface or the like symmetrical surface, so that the beam spreading effect occurs along an axis orthogonal to a cap assembly radius passing through the fiber. Likewise, each of the distal fiber ends may be provided with a convex cylindrical surface, or with converging tapered planar surfaces 47, as shown in FIG. 8, which create a short focal length beyond which the beams diverge before striking the reflective surface and the band 16. The surfaces 47 are oriented so that the beam spreading effect occurs along an axis orthogonal to a cap assembly radius passing through the fiber. In either case the beam spreading pattern at the heated band 16 is substantially as shown in FIG. 6.

With reference to FIGS. 9 and 10, another embodiment of the invention directed toward spreading the laser beams emanating from the optical fibers 37 includes optical surfaces formed in the planar end face 14 of the substrate member 11. A pair of shallow grooves 48 and 49 are machined or otherwise formed in the end face 14, the grooves being mutually orthogonal and intersecting at the axis of the bore 12. Each groove is formed of a pair of generally smooth surfaces 51 and 52 which extend into the substrate member 11 and converge to define a shallow V configuration. The grooves are positioned to be centered with respect to the incident laser beams 53 from the optical fibers 37. The V-shaped surfaces 51 and 52 act as minus lens, as shown in FIG. 9, spreading each incident beam along an axis perpendicular to a cap assembly radius extending colinear with the respective groove. The resulting beam spreading pattern is substantially as shown in FIG. 6. It may be appreciated that the beam spreading techniques shown in FIGS. 7–10 may be used individually or combined as required to provide uniform heating throughout the band 16, without affecting the vectorized heating capability of the device.

With regard to FIG. 11, a further embodiment of the invention comprises a laser heated cautery cap which is also based on a transparent substrate member 56 formed in a closed curved configuration such as a sphere, prolate spheroid, ellipsoid, or the like. The outer surface of the substrate member 56 is coated with a thin film of opaque material to retain all incident light within the member. A nose piece 58 includes a rounded distal end flaring to a cup-like opening adapted to receive the distal end of the substrate member 56 in a complementary fit. A jacket formed of a thin film metallization layer may be formed continuously about the outer surfaces of the nose piece 58 and the exposed outer surface of the substrate member 56 to joint the components and form a smooth outer contour. The nose piece may be hollow, or may be a solid formed of metal, ceramic, or the like.

The proximal end of the substrate member is joined to the distal end of a catheter assembly 61 by technique discussed with respect to previous embodiments. The proximal end further includes a conical cavity 59 extending therein, the axis of the conical shape generally coincident with the center portion of the substrate member. An optical fiber 62 within the catheter assembly 61 is disposed to direct a beam of laser light toward the conical cavity 59, the fiber 62 being aligned generally coaxially with the cavity 59. The beam from the fiber 62 is refracted by the conical surface, thereby directing almost all of the light energy to an annular zone 63 at the surface of the substrate member. This zone may be provided with a surface coating of light absorptive material, as described with respect to the previous embodiment, so that the incident light energy is converted to thermal energy. It may be appreciated that the width of the beam emanating from the optical fiber determines the width of the heated annular zone 63, and that the position of the zone 63 with respect to the distal end of the assembly is determined by the angle of the conical cavity 59.

The laser heated cautery cap assembly of FIG. 11 provides a very low thermal mass that is heated by a single optical fiber. Although the device is not provided with vectorized heating capability, the simple construction and assembly and the uniform heating throughout the annular band 63 provides low cost and great utility in many revascularization procedures.

We claim:

1. An improved intravascular cautery cap assembly for recanalization of a lumen, including a substrate member formed of a transparent high temperature tolerant material, said substrate member having a diameter and an outer surface which is smoothly curved along a direction axial to said substrate member, at least one optical fiber having an input end adapted to be connected to a controlled laser light source and an output end mechanically and optically coupled to said substrate member, a central bore having a surface extending axially through said substrate member and having a distal end, a counterbore extending axially into the distal end of said bore, said counterbore having a smooth, inwardly tapering surface, reflective surface coating means secured to said inwardly tapering surface to form an internally reflective surface in confronting alignment to said optical fiber output end, heat zone means at the outer surface of said substrate member and disposed to receive a primary reflection of said laser light from said internally reflective surface, said heat zone means including absorptive surface coating means which has a thermal mass for absorbing said laser light and generating thermal energy therefrom, said heat zone means being positioned on said outer surface to contact material blocking the lumen in which the substrate member is disposed.

2. The laser heated cautery cap assembly of claim 1, wherein said reflective surface coating means extends to cover the surface of said central bore.

3. The laser heated cautery cap assembly of claim 1, wherein said reflective surface coating means extends to cover all portions of said outer surface not occupied by said heat zone means.

4. The laser heated cautery cap assembly of claim 1, wherein said heat zone means includes an annular band extending about said substrate member.

5. The laser heated cautery cap assembly of claim 4, wherein said annular band is disposed directly adjacent to said counterbore surface and generally concentric therewith.

6. The laser heated cautery cap assembly of claim 1, wherein said substrate member includes a planar face in confronting relationship to said output end of said at least one optical fiber.

7. The laser heated cautery cap assembly of claim 6, further including at least one optical surface formed in said planar face, said optical surface including shaped surface means for spreading the laser light from said optical fiber in an angularly diverging manner about the axis of said substrate member.

8. The laser heated cautery cap assembly of claim 7, wherein said at least one optical surface includes at least one groove formed in said planar face, said groove having the concave configuration.

9. The laser heated cautery cap assembly of claim 8, wherein said groove is provided with a shallow V configuration.

10. The laser heated cautery cap assembly of claim 9, further including a pair of grooves disposed in orthogonal relationship and having a point of intersection generally coincident with the axis of said bore.

11. The laser heated cautery cap assembly of claim 1, wherein said substrate member is formed of sapphire.

12. The laser heated cautery cap assembly of claim 1, including a plurality of optical fibers each having an input end connected to a controlled laser light source and an output end coupled to said substrate member, said output end including optical surface means for effecting non-uniform spreading of the light beam emanating from said output end to enlarge said beam along an axis orthogonal to the axis of said central bore and orthogonal to a radius from the central bore passing therethrough.

13. The laser heated cautery cap assembly of claim 12, wherein said optical surface means includes a minus cylinder lens formed in each of said output ends.

14. The laser heated cautery cap assembly of claim 12, wherein said optical surface means includes a positive lens with cylindrical characteristics formed in each of said output ends.

15. The laser heated cautery cap assembly of claim 1, further including a nose piece, said nose piece including a proximal end portion having a tapering surface which fits in said counterbore in close tolerance fit, and means for securing said nose piece to said substrate member.

16. The laser heated cautery cap assembly of claim 15, wherein said nose piece further includes a central bore extending therethrough, said central bore of said nose piece and said central bore of said substrate member being in axial alignment.

17. The laser heated cautery cap assembly of claim 16, further including a sleeve member dimensioned to extend through both said central bores and to be secured therein in close tolerance fit, said sleeve member extending through said central bores to join mechanically said substrate member and said nose piece.

18. The laser heated cautery cap assembly of claim 16, wherein said substrate member includes a proximal end opposite said distal end thereof, and further includes a connector member secured in confronting relationship to said proximal end of said substrate member.

19. The laser heated cautery cap assembly of claim 18, wherein said connector member includes a central bore extending therethrough aligned with the central bores of said substrate member and said nose piece, said sleeve member extending through all said central bores to join mechanically said substrate member, said nose piece, and said connector member.

20. The laser heated cautery cap assembly of claim 19, wherein said connector member includes at least one hole extending therethrough parallel to the direction of said central bore, said hole being dimensioned to receive and secure said at least one optical fiber.

21. The laser heated cautery cap assembly of claim 20, wherein said connector member includes a plurality of said holes, and said assembly includes a like plurality of said optical fibers.

22. The laser heated cautery cap assembly of claim 21, wherein each of said plurality of optical fibers is directed to a respective portion of said internally reflective counterbore surface, whereby a respective portion of said heat zone means is illuminated and heated by each of said optical fibers.

23. The laser heated cautery cap assembly of claim 15, wherein said nose piece includes a distal end portion having a diameter narrower than the diameter of said substrate member.

24. The laser heated cautery cap assembly of claim 23, wherein said distal end portion is generally cylindrical in outer configuration, with a rounded distal end terminus.

25. The laser heated cautery cap assembly of claim 23, wherein said nose piece includes a medial portion extending from said distal end portion toward said proximal end portion and flaring outwardly theretoward with a smoothly contoured surface.

26. The laser heated cautery cap assembly of claim 20, wherein said connector member includes a neck portion extending proximally therefrom, said neck portion excluding means for securing an outer catheter tube to said laser heated cautery cap assembly.

27. The laser heated cautery cap assembly of claim 18, further including an outer layer applied over said smoothly curved outer surface of said substrate member and over the reflective coating means and absorptive coating means thereof, said outer layer extending over the outer surfaces of said nose piece and said connector member to form a smooth continuous outer surface over the entire assembly.

28. The laser thermal cautery cap assembly of claim 16, wherein said reflective surface coating means, said absorptive surface coating means, and said outer layer comprise thin film depositions to minimize the heated mass of said assembly.

29. The laser heated cautery cap assembly of claim 19, wherein said sleeve member is dimensioned to secure a distal end of an inner catheter tube, said inner catheter tube defining a lumen through which a guide wire may translate freely.

30. An improved intravascular cautery cap assembly for recanalization of a lumen, including a substrate member formed of a transparent, high temperature tolerant material, said substrate member having an outer surface which is smoothly curved along a direction axial to said substrate member, an optical fiber having an input end adapted to be connected to a controlled laser light source and an output end mechanically and optically coupled to said substrate member, heat zone means at the outer surface of said substrate member and disposed to receive said laser light from said output end, said heat zone means including absorptive surface coating means to absorb said laser light and generate thermal energy therefrom, said heat zone means being positioned on said outer surface to contact material blocking the lumen in which the assembly is disposed, and opaque surface coating means secured to at least all non-heat zone portions of said smoothly curved outer surface.

31. The laser heated cautery cap assembly of claim 30, wherein said substrate member includes an input surface in confronting relationship to said optical fiber output end, said input surface including means for directing said laser light from said output end of said optical fiber to said heat zone means.

32. The laser heated cautery cap assembly of claim 31, wherein said means for directing said laser light includes a concave recess formed in said input surface and defining refractive means for directing said laser light to said heat zone means.

33. The laser heated cautery cap assembly of claim 32, wherein said concave recess includes a conical conformation having an axis of symmetry passing through a central portion of said substrate member.

34. The laser heated cautery cap assembly of claim 31, wherein said substrate member includes a distal end opposite said input surface, and further including a nose piece secured to said distal end portion of said substrate member.

35. The laser heated cautery cap assembly of claim 34, wherein said nose piece include a narrow, rounded distal tip portion and a flaring proximal portion defining an opening mating in complementary fit fashion with said substrate member.

* * * * *